US012129313B2

(12) United States Patent
Samuelsson et al.

(10) Patent No.: US 12,129,313 B2
(45) Date of Patent: *Oct. 29, 2024

(54) ANTI-INFLAMMATORY USE OF PEPTIDE (71) Applicant: ENLITISA (SHANGHAI) PHARMACEUTICAL CO., LTD, Shanghai (CN)

(72) Inventors: Bengt Ingemar Samuelsson, Stockholm (SE); Ming Gu, Jiangyin (CN)

(73) Assignee: ENLITISA (SHANGHAI) PHARMACEUTICAL CO., LTD., Shanghai (CN)

(*) Notice: Subject to any disclaimer, the term of this patent is extended or adjusted under 35 U.S.C. 154(b) by 0 days.

This patent is subject to a terminal disclaimer.

(21) Appl. No.: 17/350,795

(22) Filed: Jun. 17, 2021

(65) Prior Publication Data
US 2021/0317166 A1    Oct. 14, 2021

Related U.S. Application Data (63) Continuation of application No. 16/628,181, filed as application No. PCT/CN2018/094440 on Jul. 4, 2018, now Pat. No. 11,059,859.

(30) Foreign Application Priority Data

Jul. 5, 2017  (WO) ............... PCT/CN2017/091818

(51) Int. Cl.
| A61K 38/08 | (2019.01) |
| A61K 38/00 | (2006.01) |
| A61K 38/10 | (2006.01) |
| A61P 17/00 | (2006.01) |
| C07K 7/06  | (2006.01) |
| C07K 7/08  | (2006.01) |

(52) U.S. Cl.
CPC ............... *C07K 7/06* (2013.01); *A61P 17/00* (2018.01); *A61K 38/00* (2013.01)

(58) Field of Classification Search
CPC .... A61K 38/00; A61K 38/1767; A61K 38/08; A61K 38/10; A61P 17/00; C07K 7/06; C07K 7/08
See application file for complete search history.

(56) References Cited

U.S. PATENT DOCUMENTS

| 5,616,311 A | 4/1997 | Yen |
| 6,127,166 A * | 10/2000 | Bayley ............. C07K 14/43504 435/325 |
| 6,987,170 B1 | 1/2006 | Silverman et al. |
| 2018/0228873 A1 | 8/2018 | Samuelsson |
| 2018/0243371 A1 | 8/2018 | Gao |
| 2020/0148722 A1 | 5/2020 | Samuelsson |

FOREIGN PATENT DOCUMENTS

| CA | 2992315 A1 * | 1/2017 | .......... A61K 35/618 |
| WO | 81/03124 | 11/1981 | |
| WO | WO 88/05654 * | 8/1988 | ............... A61K 7/48 |
| WO | 96/39128 | 12/1996 | |
| WO | 2014186937 A1 | 11/2014 | |
| WO | 2015070814 A1 | 11/2014 | |
| WO | 2017011982 A1 | 1/2017 | |
| WO | 2017/028025 A1 | 2/2017 | |
| WO | 2017/181372 A1 | 10/2017 | |
| WO | 2019/011286 A1 | 1/2019 | |

OTHER PUBLICATIONS

WO 88/05654 Google translate, pp. 1-5. Aug. 1988. (Year: 1988).*
International Search Report and Written Opinion for Application No. PCT/CN2018/094440 (dated Sep. 26, 2018).
Filpula, David R., et al., "Structural and Functional Repetition in a Marine Mussel Adhesive Protein," Biotechnol. Prog., 6(3):171 (1990).
Burzio and Waite, "Cross-Linking in Adhesive Quinoproteins: Studies with Model Decapeptides", Biochemistry 39:11147-11153 (2000).
Dalsin et al, "Mussel Adhesive Protein Mimetic Polymers for the Preparation of Nonfouling Surfaces", J. Am. Chem. Soc, 125:4253-4258 (2003).
Gao et al, "Review on Mussel Adhesive Protein", Journal of Anhui Agr. Sci. 39(32):19860-19862 (2011).
Waite et al, "Nature's Underwater Adhesive Specialist", Int. J. Adhesion and Adhesives 7(1):9-14 (1987).
Yamamoto et al, "Synthesis and Adhesive Studies of Marine Polypeptides", J. Chem. Soc., Perkin Trans. 1:613-618 (1987).
Zhu et al, "Composition, Working Mechanism and Application of Mussel Adhesive Protein", Translation Advances in Marine Science 32(4):560-570 (2014).
International Search Report and Written Opinion for Application No. PCT/CN2017/091818 (dated Apr. 8, 2018).
Kanyalkar et al., "Conformation of a Model Peptide of the Tandem Repeat Decapeptide in Mussel Adhesive Protein by NMR and MD Simulations," Biomat. 23(2):389-396 (2002).
Belli et al., "Abstracts from the Academy of Dental Materials Conference in Portland, Oct. 2009," Dental Materials 26:e125 (2010).
Bhattacharjee et al., "Bioadhesive Analogue Polypeptides Containing L-Dopa Residues: Synthesis, Polymerization and Adhesive Properties," Polym. Mat. Sci. Eng. 59:110-114 (1988).
Lu et al., "Facial Corticosteroid Addictive Dermatitis in Guiyang City, China," Clin. Exp. Dermatol. 35(6): 618-620 (2009).
Olivieri et al., "Surface Properties of Mussel Adhesive Protein Component Films," Biomaterials 13(14):1000-1008 (1992).

(Continued)

*Primary Examiner* — Julie Ha
(74) *Attorney, Agent, or Firm* — Troutman Pepper Hamilton Sanders LLP (Rochester)

(57) ABSTRACT

Provided a peptide of the sequence Ala-Lys-Pro-Ser-Tyr-Hyp-Hyp-Thr-DOPA-Lys or a salt thereof for use in the treatment of inflammation, of an inflammatory disorder and/or of ion thea condition characterized by inflammation, including wounds, burns, psoriasis, acne and atopic dermatitis.

14 Claims, 3 Drawing Sheets

Specification includes a Sequence Listing.

(56) References Cited

OTHER PUBLICATIONS

Xiao et al., "Rebounding Triad (Severe Itching, Dryness and Burning) After Facial Corticosteroid Discontinuation Defines a Specific Class of Corticosteroid-Dependent Dermatitis," J. Dermatol. 42(7):697-702 (2015).

Kaushik et al., "Biomedical and Clinical Importance of Mussel-Inspired Polymers and Materials," Mar. Drugs 13(11):6792-6817 (2015).

Perikamana et al., "Materials from Mussel-Inspired Chemistry for Cell and Tissue Engineering Applications," Biomacromolecules 16(9):2541-2555 (2015).

Cowan, D., "The Marine Biosphere: A Global Resource for Biotechnology," Trends Biotechnol. 15(4):129-131 (1997).

Inflammatory disorders from Merck Manual, pp. 1-4. Accessed Aug. 30, 2020. (Year: 2020).

Dermatitis from Merck Manual, pp. 1-4. Accessed Aug. 30, 2020. (Year: 2020).

Inflammation from Merck Manual, pp. 1-3. Accessed Aug. 30, 2020. (Year: 2020).

Waite, J.H., "Evidence for a Repeating 3,4-Dihydroxyphenylalanine- and Hydroxyproline-containing Decapeptide in the Adhesive Protein of the Mussel, *Mytilus edulis* L.," J. Biol. Chem. 258(5):2911-15 (1983).

\* cited by examiner

SEQUENCE LISTING

```
<160> NUMBER OF SEQ ID NOS: 1

<210> SEQ ID NO 1
<211> LENGTH: 10
<212> TYPE: PRT
<213> ORGANISM: Artificial Sequence
<220> FEATURE:
<223> OTHER INFORMATION: Protein
<220> FEATURE:
<221> NAME/KEY: MISC_FEATURE
<222> LOCATION: (6)..(6)
<223> OTHER INFORMATION: Xaa at position 6 is 3-hydroxyproline or
      4-hydroxyproline
<220> FEATURE:
<221> NAME/KEY: MISC_FEATURE
<222> LOCATION: (7)..(7)
<223> OTHER INFORMATION: Xaa at position 7 is 3-hydroxyproline or
      4-hydroxyproline
<220> FEATURE:
<221> NAME/KEY: MISC_FEATURE
<222> LOCATION: (9)..(9)
<223> OTHER INFORMATION: Xaa at position 9 is dihydroxyphenylalanine

<400> SEQUENCE: 1

Ala Lys Pro Ser Tyr Xaa Xaa Thr Xaa Lys
1               5                   10
```

ANTI-INFLAMMATORY USE OF PEPTIDE

This application is a continuation of U.S. patent application Ser. No. 16/628,181, filed Jan. 2, 2020, which is a national stage application under 35 U.S.C. § 371 of PCT Application No. PCT/CN2018/094440, filed Jul. 4, 2018, which claims the priority benefit of PCT Application No. PCT/CN2017/091818, filed Jul. 5, 2017.

FIELD OF THE INVENTION

This invention relates to the new use of a known compound.

BACKGROUND AND PRIOR ART

Inflammation is typically characterised as a localised tissue response to e.g. invasion of microorganisms, certain antigens, damaged cells or physical and/or chemical factors. The inflammatory response is normally a protective mechanism which serves to destroy, dilute or sequester both the injurious agent and the injured tissue, as well as to initiate tissue healing.

Inflammation may result from physical trauma, infection, some chronic diseases (e.g. psoriasis and autoimmune diseases, such as rheumatoid arthritis) and/or chemical and/or physiological reactions to external stimuli (e.g. as part of an allergic response). A complex series of events may be involved, in which inflammatory mediators increase blood flow and dilation of local blood vessels, resulting in redness and heat, the exudation of fluids, often resulting in localised swelling, leukocytic migration into the inflamed area, and pain.

Many conditions/disorders are characterized by, and/or are caused by, abnormal, tissue-damaging inflammation. Such conditions are typically characterized by activation of immune defence mechanisms, resulting in an effect that is more harmful than beneficial to the host, and are generally associated with varying degrees of tissue redness or hyperemia, swelling, hyperthermia, pain, itching, cell death, tissue destruction, cell proliferation and/or loss of function. Examples include inflammatory bowel diseases, rheumatoid arthritis, multiple sclerosis, psoriasis, glomerulonephritis and transplant rejection.

Typically, a complex series of events results in inflammatory changes such as increased blood flow through dilation of local blood vessels, resulting in redness and heat, the extravasation of leukocytes and plasma, often resulting in localised swelling, activation of sensory nerves (resulting in pain in some tissues) and loss of function. These inflammatory changes are triggered by a cascade of cellular and biochemical events involving cells like neutrophils, monocytes, macrophages and lymphocytes together with inflammatory mediators such as vasoactive amines, cytokines, complement factors and reactive oxygen species.

Amongst other things, inflammation plays a key role in the wound healing process. Wounds and burns can therefore be classified as conditions with which inflammation is associated. Traditional thinking in the art is that antiinflammatory drugs should not be applied directly to open wounds, as this would be detrimental to the progress of wound healing.

Mussel adhesive protein (MAP), also known as *Mytilus edulis* foot protein (mefp), is a protein secreted by marine shellfish species, such as *Mytilus edulis, Mytilus coruscus* and *Perna viridis*. The adhesive protein is secreted by mussels from the byssus gland where it is produced and stored. When secreted on a surface of a solid, such as a rock, but also other solid objects, such as metals, wood, glass, etc., a water-proof bond is formed which fixes the mussel to the solid object. Mussels are typically attached, in groups, to coastal reefs or to the bottoms of ships. The bond is incredibly strong, having the ability to resist wave impacts in coastal waters.

Studies on *Mytilus edulis, Mytilus galloprovincialis, Mytilus californias* and *Perna viridis* have thus far identified eleven separate adhesive protein subtypes derived from mussels: mfp-1 (sometimes referred to as "mefp-1", hereinafter used interchangeably), mfp-2/mefp-2, mfp-3/mefp-3, mfp-4/mefp-4, mfp-5/mefp-5, mfp-6/mefp-6; the collagens pre-COL-P, pre-COL-D and pre-COL-NG; and the mussel feet matrix proteins PTMP (proximal thread matrix protein), and DTMP (distal proximal thread matrix protein). See, for example, Zhu et al, *Advances in Marine Science*, 32, 560 (2014) and Gao et al, *Journal of Anhui Agr. Sci.*, 39, 19860 (2011)).

All mussel adhesive proteins, including sub-types thereof, have two structural characteristics, in that they comprise: (1) lysine, such that the protein carries a high positive charge loading (due to the $NH_2$ termini); (2) 3,4-dihydroxyphenylalanine (DOPA, dopamine), the catechol part of which is responsible for the formation of strong covalent bonds and consequently the ability of mussel adhesive proteins to bind to solid surfaces.

Products based on mussel adhesive protein products are presently used in a limited number of fields (including micro-cellular bonding, as tissue bonding agents and the treatment of wounds and burns). Commercial products are either directly used as a solution of mussel adhesive protein or are stored as a freeze-dried powder for dissolution prior to use.

The decapeptide of the sequence: Ala-Lys-Pro-Ser-Tyr-Hyp-Hyp-Thr-DOPA-Lys (also referred to hereinafter to as "MAP Peptide") is a pharmaceutically-acceptable low molecular weight derivative of MAP, that was first disclosed by Waite in *Int. J. Adhesion and Adhesives*, 7, 9 (1987). MAP Peptide may derived and/or isolated as a low molecular weight derivative of naturally-occurring MAPs, or may be synthesized, for example, as described by Yamamoto in *J. Chem. Soc., Perkin Trans.* 1, 613 (1987). See also Dalsin et al, *J. Am. Chem. Soc.*, 125, 4253 (2003).

To the applicant's knowledge, the use of MAP Peptide in the treatment of inflammation or inflammatory disorders is not disclosed in the prior art.

DISCLOSURE OF THE INVENTION

According to the invention, there is provided the (isolated) peptide compound of the sequence Ala-Lys-Pro-Ser- Tyr-Hyp-Hyp-Thr-DOPA-Lys (MAP Peptide), or a salt thereof, for use in the treatment of inflammation.

Salts of MAP Peptide that may be mentioned include pharmaceutically-acceptable salts, and cosmetically-acceptable salts, such as pharmaceutically- or cosmetically-acceptable acid addition salts and base addition salts. Such salts may be formed by conventional means, for example by reaction of free peptide with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of active ingredient in the form of a salt with another counter-ion, for example using a suitable ion exchange resin.

Preferred salts include, for example, hydrochloride, bisulfate, maleate, mesylate, tosylate, alkaline earth metal salts, such as calcium and magnesium, or alkali metal salts, such as sodium and potassium salts.

MAP Peptide and salts thereof are useful because they possess biological (e.g. pharmacological) activity. Thus, MAP Peptide/salts are useful as human and animal medicine. They are therefore indicated as pharmaceuticals (and/or in veterinary science), although they may also be used as cosmetics and/or as part of a medical device.

Although MAP Peptide/salts may possess pharmacological activity as such, certain pharmaceutically-acceptable (e.g. "protected") derivatives thereof may exist or may be prepared which may not possess such activity, but which may be administered and thereafter be metabolised or chemically transformed to form MAP Peptide. Such compounds (which may possess some pharmacological activity, provided that such activity is appreciably lower than that of the active compounds to which they are metabolised/transformed) may therefore be described as "prodrugs" of MAP Peptide.

As used herein, references to prodrugs will include compounds that form MAP Peptide, in an experimentally-detectable amount, within a predetermined time, following administration. All prodrugs of MAP Peptide are included within the scope of the invention.

The "treatment of inflammation" includes the treatment of inflammation in any organ of the body (including soft tissue, joints, nerves, the vascular system, internal organs, especially mucosal surfaces, and particularly the skin), irrespective of the cause, and also includes all such inflammatory disorders or conditions, and/or disorders or conditions characterized by inflammation (e.g. as a symptom).

Inflammatory conditions may be (and are typically) characterized by activation of immune defence mechanisms, resulting in an effect that is more harmful than beneficial to the host. Such conditions are generally associated with varying degrees of tissue redness or hyperemia, swelling, hyperthermia, pain (including aching), exudation of body fluids, itching (pruritis), cell death and tissue destruction, cell proliferation, and/or loss of function.

Inflammatory conditions that may be mentioned include arteritis, diabetes mellitus, metabolic syndrome, rosacea, asthma and allergy, ankylosing spondylitis, chronic obstructive pulmonary disease, gouty arthritis, inflammatory bowel disease (such as Crohn's disease and ulcerative colitis), multiple sclerosis, osteoarthritis, pancreatitis, prostatitis, psoriatic arthritis, rheumatoid arthritis, tendinitis, bursitis, Sjogren's syndrome, systemic lupus erythematosus, uveitis, urticaria, vasculitis, mastocytosis, diabetic vascular complications, migraine, atherosclerosis and associated cardiovascular disorders. A disease state that may be specifically mentioned is chronic obstructive pulmonary disease (COPD).

Inflammatory conditions that may be more especially mentioned include inflammations of the skin or mucosa (including the oral, nasal, ocular, vaginal, cervical and/or anorectal mucosae, more particularly the oral or nasal mucosae), such as inflammation resulting from infections (such as viral and/or bacterial infections), or allergic/atopic conditions (such as rhinitis, pharyngitis, periodontitis, gingivitis, xerophthalmia, conjunctivitis, dermatitis, urticaria (hives) and food allergy); and other inflammatory conditions, such as herpes, drug eruptions, polymorphous light eruptions, sunburn, early manifestations of skin cancers (erythema-like skin lesions), pathological hair loss (including following skin grafting), chemo rash, psoriasis, erythema multiforme, folliculitis, eczema and external otitis. A disease state that may be specifically mentioned is polymorphous light eruptions.

More particularly, MAP Peptide and salts thereof may be used to treat certain conditions characterized by inflammation, and/or with which inflammation is associated. Such conditions may include wounds (including abrasions (scratches), incisions (including operative incisions), lacerations, punctures, avulsions, bruising and scarring), burns (including inflammation resulting from surgery following burns, such as skin grafting) and other conditions, such as hemorrhoids.

Wounds of the skin or mucosa may arise from internal or external physical injury to the membrane surface, or may be caused by (i.e. be a symptom of an underlying physiological disorder).

Physical (e.g. "open") wounds may be caused by sharp objects (cuts, incisions, punctures) or blunt objects/mechanical forces (lacerations, abrasions, avulsions), physical blows (bruises), heat or chemicals (burns and blisters), UV light (sunburn), cold (chilblains or frostbite). Wounds may be superficial (damage only to the epidermis and/or dermis) or may be full thickness wounds (damage below the epidermis and/or dermis). In serious cases, subcutaneous and/or submucosal tissues, such as muscles, bones, joints, and even internal organs, may be damaged.

MAP Peptide and salts thereof may be used to treat not only the inflammation, pain (including aching) and/or pruritis (itching) associated with the wound itself and the healing process, but also they may be used to prevent the exudation of body fluids from wounds, the risk of infection, and also the prevention of physiological reactions that result from inflammation and/or wound healing processes, such as scarring and melanin pigmentation.

Scarring is a consequence of inflammation and/or wound healing and is a general term for the formation of fibrotic tissue that is a consequence of such inflammation/healing.

MAP Peptide and salts thereof may also be useful in the suppression of the production of melanin pigmentation that may result from inflammation and/or wound healing. MAP Peptide and salts thereof may also be useful in the suppression of disorders associated with melanin pigmentation, such as chloasma, freckles, melanosis, malar rash and other chromatosis, skin cancers with melanoma, and chromatosis that is caused by exposure to the sun or skin diseases like acne.

Wounds may also arise as a consequence of diseases or disorders. Such may include blistering and/or ulcers of the skin and mucosa. These are common conditions that are often long-lasting and difficult to treat. Skin tissues can often be damaged, removed, liquefied, infected and/or necrotic.

Ulcers can lead to secondary consequences to health particularly if they become infected, are hard to heal and are costly. They can also cause significant psychological stress and economic loss to patients, affecting both general well-being and quality of life.

In the alternative, inflammatory skin conditions or diseases in which MAP Peptide and salts thereof find particular utility include psoriasis, acne, eczema and dermatitis, especially allergic/atopic dermatitis.

Psoriasis is a chronic, inflammatory skin disease with a tendency to recur (some patients never heal during their entire life). Clinical manifestations of psoriasis mainly include erythema and scales. It can occur over the whole body, but is more commonly observed on the scalp and limbs.

Acne is a follicular (pilosebaceous unit) chronic, inflammatory skin disease, the occurrence of which is closely related to main factors like hypersteatosis, blocked pilosebaceous ducts (including closed and open comedones), bacterial infection and inflammatory reactions, that tends to occur during youth, characterised by multiform skin lesions on the face. The term acne thus includes regular acne and acne rosacea (i.e. copper nose).

Eczema is a skin inflammatory reaction with strong itching caused by a variety of internal and external factors. It has three phases, acute, sub-acute, and chronic. In the acute phase, there is a tendency for the production of exudates, while the chronic phase includes infiltration and hypertrophy. Skin lesions are often itchy and recur easily.

Dermatitis is a common skin disease characterised by coarseness, redness, itching, eczema, and dryness. Small lumps, refractory ulcers, and pigmented spots caused by dermatitis may, if not treated promptly, develop to basal cell carcinoma, squamous cell carcinoma, and malignant melanoma. Dermatitis may be caused by various internal and external infectious or non-infectious factors, including substances (contact dermatitis) or allergy (allergic/atopic dermatitis). Also included is seborrheic dermatitis (seborrheic eczema) and all forms of steroid-dependent dermatitis (including light-sensitive seborrheid, perioral dermatitis, rosacea-like dermatitis, steroid-rosacea, steroid-induced rosacea, iatrosacea, steroid dermatitis resembling rosacea, topical corticosteroid-induced rosacea-like dermatitis and, more particularly, facial corticosteroid addictive dermatitis (FCAD) or facial corticosteroid-dependent dermatitis (FCDD), as characterised by flushing, erythema, telangiectasia, atrophy, papules and/or pustules in the facial area after long-term treatment with (including uncontrolled use, abuse or misuse of) topical corticosteroids; see, for example, Xiao et al, *J. Dermatol.*, 42, 697 (2015) and Lu et al, *Clin. Exp. Dermatol.*, 35, 618 (2009)).

It has been found that MAP Peptide and salts thereof may have positive effects in mitigating erythema, redness and swelling, edema, blisters, and bullous pemphigoid caused by various conditions including those mentioned generally and specifically herein, and may inhibit exudation of subcutaneous tissue fluid, and suppressing itching and pain caused by such inflammatory conditions.

Other inflammatory conditions that may be mentioned include:

(a) Mucosal inflammation, such as oral mucositis, apthous ulcers, otitis media, laryngitis, tracheitis, esophagitis, gastritis, enteritis and enterocolitis (including bacillary dysentery, chronic amoebic dysentery, schistosomiasis, nonspecific ulcerative colitis and regional enteritis), cervicitis and endocervicitis, endometritis, inflammation caused by inhalation injury and the like, as well as mucosal inflammation associated with cancers, and infections (e.g. viral infections, such as the common cold or influenza), that affect mucosal surfaces, such as those in the oral cavity, the nasopharynx, the ear, the throat, the trachea, the gastrointestinal tract, the cervix, etc.

(b) Orthopedic inflammation associated with, for example bone fractures, pyogenic infection of bones and joints, inflammation caused by rheumatic bone diseases, as well as pyogenic osteomyelitis (acute, chronic, localized, sclerotic, post-traumatic), pyogenic arthritis, bone tumors (osteoma, osteoid osteoma, chondroma), bone cysts, osteoclastoma, primary bone sarcoma (osteosarcoma, chondrosarcoma, osteofibrosarcoma, Ewing's sarcoma, non-Hodgkin's lymphoma, myeloma, chordoma), metastatic bone tumors, tumor-like lesions of bone (bone cyst, aneurysmal bone cyst, eosinophilic granuloma, fibrous dysplasia); and rheumatic arthritis.

(c) Nerve inflammation, such as peripheral polyneuritis, facial neuritis, peripheral neuritis, subcutaneous neuritis, ulnar neuritis, intercostal neuritis, etc.

(d) Subcutaneous and submucosal soft tissue inflammation, such as myositis, ligamentitis, tendonitis, panniculitis capsulitis, lymphadenitis, bubonadenitis, tonsillitis, synovitis, fasciitis, and soft tissue inflammation caused by injuries, contusion or laceration of muscles, ligaments, fascia, tendons, membrana synovialis, fat, articular capsules, and lymphoid tissue.

(e) Vascular inflammation, such as allergic leukocytoclastic vasculitis, allergic cutaneous vasculitis, polyarteritis nodosa, thrombotic vasculitis, granulomatous vasculitis, lymphocytic vasculitis, vasculitis with abnormalities in blood composition, and rheumatic vasculitis, as well as vascular inflammation associated with vascular cancers caused by allergic leukocytoclastic vasculitis, polyarteritis nodosa, thrombotic vasculitis, granulomatous vasculitis, lymphocytic vasculitis, vasculitis with abnormalities in blood composition, and rheumatic vasculitis.

(f) Inflammation of the internal organs, such as the heart, stomach, intestine, lung, liver, spleen, kidney, pancreas, bladder, ovary, and prostate, including but not limited to pericarditis, myocarditis, endocarditis, pneumonia, hepatitis, splenitis, nephritis pancreatitis, cystitis, oophoritis, prostatitis and treatment of gastric ulcer.

According to a further aspect of the invention there is provided a method of treatment of inflammation, of an inflammatory disorder, and/or of a disorder/condition characterized by inflammation (for example as a symptom), which method comprises the administration of MAP Peptide or a salt thereof to a patient in need of such treatment.

For the avoidance of doubt, in the context of the present invention, the terms "treatment", "therapy" and "therapy method" include the therapeutic, or palliative, treatment of patients in need of, as well as the prophylactic treatment and/or diagnosis of patients which are susceptible to, inflammation and/or inflammatory disorders.

"Patients" include reptilian and, preferably, mammalian (particularly human) patients.

In accordance with the invention, MAP Peptide/salts are preferably administered locally or systemically, for example orally, intravenously or intraarterially (including by intravascular and other perivascular devices/dosage forms (e.g. stents)), intramuscularly, cutaneously, subcutaneously, transmucosally (e.g. sublingually or buccally), rectally, intravaginally, transdermally, nasally, pulmonarily (e.g. tracheally or bronchially), topically, or by any other parenteral route, in the form of a pharmaceutical preparation comprising the compound(s) in pharmaceutically acceptable dosage form(s). Administration by inhalation (e.g. nasally) is particularly useful when the condition to be treated is rhinitis or inflammation resulting from viral infections of the airways (common cold, influenza). Pulmonary administration is particularly useful when the condition to be treated is COPD. Topical forms of administration may be enhanced by creating a spray comprising active ingredients, e.g. by using a powder aerosol or by way of an aqueous mist using an appropriate atomisation technique or apparatus, such as a nebulizer.

Preferred modes of delivery of MAP Peptide/salts thereof include topically to the site of inflammation in an appropriate (for example pharmaceutically-acceptable) vehicle and/or a commercially-available formulation, but may also include oral, intravenous, cutaneous or subcutaneous, nasal, intramuscular, or intraperitoneal delivery.

MAP Peptide and salts thereof will generally be administered in the form of one or more (e.g. pharmaceutical) formulations in admixture with a (e.g. pharmaceutically acceptable) adjuvant, diluent or carrier, which may be selected with due regard to the intended route of administration and standard pharmaceutical or other (e.g. cosmetic) practice. Such pharmaceutically acceptable carriers may be chemically inert to the active compounds and may have no detrimental side effects or toxicity under the conditions of use. Such pharmaceutically acceptable carriers may also impart an immediate, or a modified, release of the active ingredient.

Suitable pharmaceutical formulations may be commercially available or otherwise prepared according to techniques that are described in the literature, for example, Remington *The Science and Practice of Pharmacy*, 22$^{nd}$ edition, Pharmaceutical Press (2012) and *Martindale—The Complete Drug Reference*, 38$^{th}$ Edition, Pharmaceutical Press (2014) and the documents referred to therein, the relevant disclosures in all of which documents are hereby incorporated by reference. Otherwise, the preparation of suitable formulations including MAP Peptide and salts thereof may be achieved non-inventively by the skilled person using routine techniques.

MAP Peptide/salt may be in the form of an aqueous formulation such as an emulsion, a suspension and/or a solution (e.g. an (optionally) buffered aqueous formulation (e.g. solution), such as a physiological saline-containing formulation (e.g. solution), a phosphate-containing formulation (e.g. solution), an acetate-containing formulation (e.g. solution) or a borate-containing formulation (e.g. solution)), or a freeze-dried powder.

Active ingredient may in the alternative be combined with appropriate excipents to prepare:

gel formulations (for which suitable gel matrix materials include cellulose derivatives, carbomer and alginates, gummi tragacanthae, gelatin, pectin, carrageenan, gellan gum, starch, Xanthan gum, cationic guar gum, agar, noncellulosic polysaccharides, vinyl polymers, acrylic resins, polyvinyl alcohol, carboxyvinyl polymer and, particularly, hyaluronic acid);

lotions (condensates; for which suitable matrix materials include cellulose derivatives, glycerin, noncellulosic polysaccharides, polyethylene glycols of different molecular weights and propanediol);

pastes or ointments (for which suitable paste matrix materials include glycerin, vaseline, paraffin, polyethylene glycols of different molecular weights, etc.);

creams or foams (for which suitable excipients (e.g. foaming agents) include hydroxypropyl methyl cellulose, gelatin, polyethylene glycols of different molecular weights, sodium dodecyl sulfate, sodium fatty alcohol polyoxyethylene ether sulfonate, corn gluten powder and acrylamide);

powder aerosols (for which suitable excipients include mannitol, glycine, dextrin, dextrose, sucrose, lactose, sorbitol and polysorbates); and/or liquid (aerosol) sprays for oral use or for inhalation (for which suitable excipients include viscosity modifiers, such as hyaluronic acid, emulsifiers, buffering agents, alcohols, water, preservatives, sweeteners, flavours, etc.).

Moisturizing agents, such as glycerol, glycerin, polyethylene glycol, trehalose, glycerol, petrolatum, paraffin oil, hyaluronic acid and salts (e.g sodium and potassium salts) thereof, octanoic/capyic triglyceride, and the like; and/or antioxidants, such as vitamins and glutathione; and/or pH modifiers, such as acids, bases and pH buffers, may also be included in such formulations, as appropriate. Furthermore, surfactants/emulsifiers, such as hexadecanol (cetyl alcohol), fatty acids (e.g. stearic acid), sodium dodecyl sulfate (sodium lauryl sulfate), sorbitan esters (e.g. sorbitan stearate, sorbitan oleate, etc.), monoacyl glycerides (such as glyceryl monostearate) polyethoxylated alcohols, polyvinyl alcohols, polyol esters, polyoxyethylene alkyl ethers (e.g. polyoxyethylene sorbitan monooleate), polyoxyethylene castor oil derivatives, ethoxylated fatty acid esters, polyoxylglycerides, lauryl dimethyl amine oxide, bile salts (e.g. sodium deoxycholate, sodium cholate), phospholipids, N,N-dimethyldodecylamine-N-oxide, hexadecyltrimethyl-ammonium bromide, poloxamers, lecithin, sterols (e.g. cholesterol), sugar esters, polysorbates, and the like; preservatives, such as phenoxyethanol, ethylhexy glycerin, and the like; and thickeners, such as acryloyldimethyltaurate/VP copolymer, may be included. In particular stearic acid, glyceryl monostearate, hexadecanol, sorbitan stearate, cetyl alcohol, octanoic/capric glyceride etc. may be included, particularly in cream formulations.

MAP Peptide/salts, and (e.g. pharmaceutical) formulations (e.g. aqueous solutions, gels, creams, ointments, lotions/condensates, foams and/or pastes as described above) including them, may further be combined with an appropriate matrix material to prepare a dressing or a therapeutic patch for application on a biological surface, such as the skin or a mucosal surface. Such formulations may thus be employed to impregnate a matrix material, such as gauze, non-woven cloth or silk paper. The therapeutic patch may alternatively be, for example, a band-aid, a facial mask, an eye mask, a hand mask, a foot mask, etc.

Vaseline may be employed for use in applying such dressings to wounds, but we have also found that ointments based on PEGs (e.g. PEG400) may be combined with matrix materials to prepare dressings without the need to use vaseline.

MAP Peptide and salts thereof may also be combined in treatment with one or more growth factors selected from platelet-type growth factors (including platelet-derived growth factors, PDGFs); osteosarcoma-derived growth factors (ODGF), epidermal growth factors (EGFs), transforming growth factors (TGFα and TGFβ), fibroblast growth factors (αFGF, βFGF), insulin-like growth factors (IGF-I, IGF-II), nerve growth factors (NGF), interleukin-type growth factors (IL-1, IL-1, IL-3), erythropoietin (EPO), and colony stimulating factor (CSF).

According to a further aspect of the invention there is provided a (e.g. pharmaceutical) composition comprising MAP Peptide of a salt thereof and one or more pharmaceutically-acceptable excipient, such as an adjuvant, diluent or carrier. Preferred compositions are for topical administration to the skin or to a mucosal surface.

Administration of active ingredients may be continuous or intermittent. The mode of administration may also be determined by the timing and frequency of administration, but is also dependent, in the case of the therapeutic treatment of inflammation, on the severity of the condition.

Depending on the disorder, and the patient, to be treated, as well as the route of administration, MAP Peptide and salts thereof may be administered at varying therapeutically effective doses to a patient in need thereof.

Similarly, the amount of active ingredient in a formulation will depend on the severity of the condition, and on the patient, to be treated, but may be determined by the skilled person.

In any event, the medical practitioner, or other skilled person, will be able to determine routinely the actual dosage, which will be most suitable for an individual patient, depending on the severity of the condition and route of administration. The dosages mentioned herein are exemplary of the average case; there can, of course, be individual instances where higher or lower dosage ranges are merited, and such are within the scope of this invention.

Doses may be administered between once and four times daily.

Appropriate concentrations of MAP Peptide or salts thereof in an aqueous solution product may be about 0.01 (e.g. about 0.1) to about 15.0 (e.g. about 1.5) mg/mL, and appropriate pH values are in the range of about 1.0 to about 7.0 (for example about 3.0 to about 6.5), in all cases calculated as the free (non-salt) peptide.

Appropriate topical doses of MAP Peptide/salts are in the range of about 0.1 to about 50 $\mu g/cm^2$ of treated area, such as about 1 to about 20 $\mu g/cm^2$ of treated area, including about 2 to about 10 $\mu g/cm^2$) of treated area, such as about 5 $\mu g/cm^2$ of treated area, in all cases calculated as the free (non-salt) peptide.

In any event, the dose administered to a mammal, particularly a human, in the context of the present invention should be sufficient to effect a therapeutic response in the mammal over a reasonable timeframe (as described hereinbefore). One skilled in the art will recognize that the selection of the exact dose and composition and the most appropriate delivery regimen will also be influenced by inter alia the pharmacological properties of the formulation, the nature and severity of the condition being treated, and the physical condition and mental acuity of the recipient, as well as the age, condition, body weight, sex and response of the patient to be treated, and the stage/severity of the disease, as well as genetic differences between patients.

In the uses and methods described herein, MAP Peptide and salts thereof may also be combined with one or more active ingredients that are useful in the treatment of inflammation and/or inflammatory disorders (other antiinflammatory agents). Such patients may thus also (and/or already) be receiving therapy based upon administration of one or more of such other active ingredients, by which we mean receiving a prescribed dose of one or more of those active ingredients mentioned herein, prior to, in addition to, and/or following, treatment with MAP Peptide/salt.

Such anti-inflammatory agents that may be used in combination with MAP Peptide/salts thereof in the treatment of inflammation include therapeutic agents that are useful in the treatment of inflammation and/or of diseases characterised by inflammation as one of its symptoms. Depending on the condition to be treated, such antiinflammatory agents may also include NSAIDs, leukotriene receptor antagonists (e.g. montelukast), corticosteroids, analgesics and certain enzymes, such as trypsin, for example as described hereinafter. MAP Peptide/salts may also be combined with leukotriene B4 (LTB4).

In this context, MAP Peptide/salts may also be combined for use in the treatment of inflammation with one or more mussel MAPs, which includes any adhesive protein that may be derived from mussel species, such as *Mytilus edulis* (blue mussel), including full length proteins, including all sub-types, that are or may be derived from mussels, such as the collagens pre-COL-P, pre-COL-D and pre-COL-NG, the mussel feet matrix proteins PTMP and DTMP, and, more preferably, mfps or mefps, such as mefp-2, mefp-3, mefp-4, mefp-5, mefp-6 and especially mefp-1, and includes mixtures or combinations of any of these proteins, such as mefps. Although mixtures/combinations of the aforementioned MAP sub-types may be provided as the MAP "component", we prefer that the purity of the principal MAP sub-type (e.g. mefp-1) is at least 25% by weight of the total amount of any such mixture.

Naturally-occurring MAPs may be prepared for example by mixed adsorption chromatography (see Chinese Patent No. ZL200710179491.0), by carboxymethyl ion exchange chromatography (see Chinese Patent No. ZL200710179492.5), and/or by salting out and dialysis (Chinese Patent No. ZL200910087567.6). Commericial sources of MAPs include USUN Bio Co. (China; sold as MAP Medical Device®), BD Biosciences (USA), Kollodis (South Korea) and Biopolymer (Sweden). MAPs may alternatively be produced using known recombinant DNA methods.

Other (e.g. pharmaceutically-acceptable) derivatives of MAPs may also be combined with MAP Peptide/salts thereof and include compounds with, for example, molecular weights in the range of about 500 Da to about 2,000 (e.g. about 1,200, such as about 800) Da. Such derivatives may also include other compounds that comprise amino acid sequences that are the same as, or are (e.g. minor) variants of, sequences that have been identified in naturally-occurring MAPs, and which may be synthesized by chemical and/or biological processes (e.g. chemical modifications of naturally-occurring MAPs, or direct synthesis). By "(e.g. minor) variants of amino acid sequences identified in naturally-occurring MAPs", we mean variations in those sequences that do not negatively affect the requisite properties of the relevant naturally-occurring MAP to a measurable degree.

Other preferred agents that may be combined MAP Peptide/salts include LTB4 (e.g. to treat wounds and burns), montelukast (e.g. to treat inflammation generally) and trypsin (e.g. to treat inflammation of the mucosa associated with e.g. viral infections).

MAP Peptide/salts may also be combined with other therapeutic agents which, when administered, are known to give rise to inflammation as a side-effect.

When MAP Peptide/salts are "combined" with other therapeutic agents in this way, the active ingredients may be administered together in the same formulation, or administered separately (simultaneously or sequentially) in different formulations.

Such combination products provide for the administration of MAP Peptide and salts thereof in conjunction with the other therapeutic agent, and may thus be presented either as separate formulations, wherein at least one of those formulations comprises a MAP Peptide/salt, and at least one comprises the other therapeutic agent, or may be presented (i.e. formulated) as a combined preparation (i.e. presented as a single formulation including MAP Peptide and the other therapeutic agent).

Thus, there is further provided:

(1) a pharmaceutical formulation including MAP Peptide or a salt thereof; another antiinflammatory agent, or agent known to give rise to inflammation as a side-effect; and a pharmaceutically-acceptable adjuvant, diluent or carrier (which formulation is hereinafter referred to as a "combined preparation"); and (2) a kit of parts comprising components:
   (A) a pharmaceutical formulation including MAP Peptide or a salt thereof in admixture with a pharmaceutically-acceptable adjuvant, diluent or carrier; and
   (B) a pharmaceutical formulation including another anti-inflammatory agent, or agent known to give rise to inflammation as a side-effect, in admixture with a pharmaceutically-acceptable adjuvant, diluent or carrier,
   which components (A) and (B) are each provided in a form that is suitable for administration in conjunction with the other.

Wherever the word "about" is employed herein, for example in the context of amounts, such as concentrations and/or doses of active ingredients, molecular weights or pHs, it will be appreciated that such variables are approximate and as such may vary by ±10%, for example ±5% and preferably ±2% (e.g. ±1%) from the numbers specified herein. In this respect, the term "about 10%" means e.g. ±10% about the number 10, i.e. between 9% and 11%.

MAP Peptide/salts thereof have the advantage that they may be used in variety of conditions characterised by inflammation, whether that condition is an organic inflammatory disease per se or is associated with, or is characterised by, inflammation (e.g. a wound, a burn or a viral infection).

The uses and methods described herein may also have the advantage that, in the treatment of the conditions mentioned hereinbefore, they may be more convenient for the physician and/or patient than, be more efficacious than, be less toxic than, have a broader range of activity than, be more potent than, produce fewer side effects than, or that it/they may have other useful pharmacological properties over, similar methods (treatments) known in the prior art for use in the treatment of inflammatory disorders or otherwise.

Figure 1A:
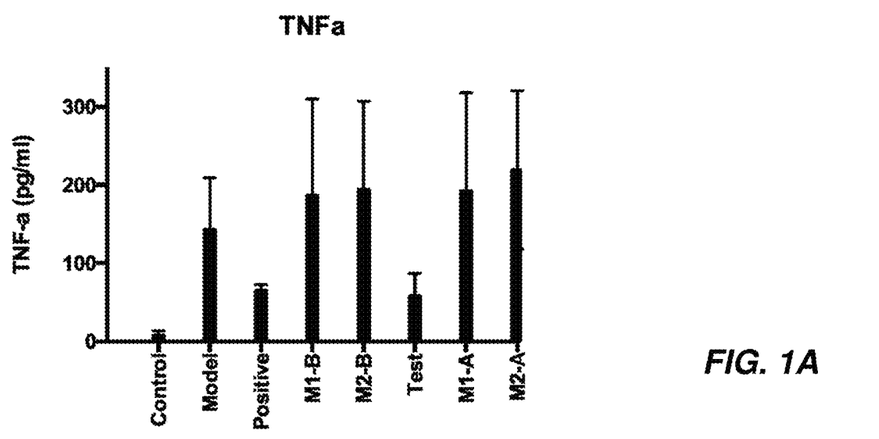
FIGS. 1A-C are graphs illustrating ELISA test results for various inflammatory markers obtained from exudates from air pouches induced in mice according to Example 1, including TNF-a (FIG. 1A), IL-6 (FIG. 1B), and IFN-γ (FIG. 1C).
Figure 1B:
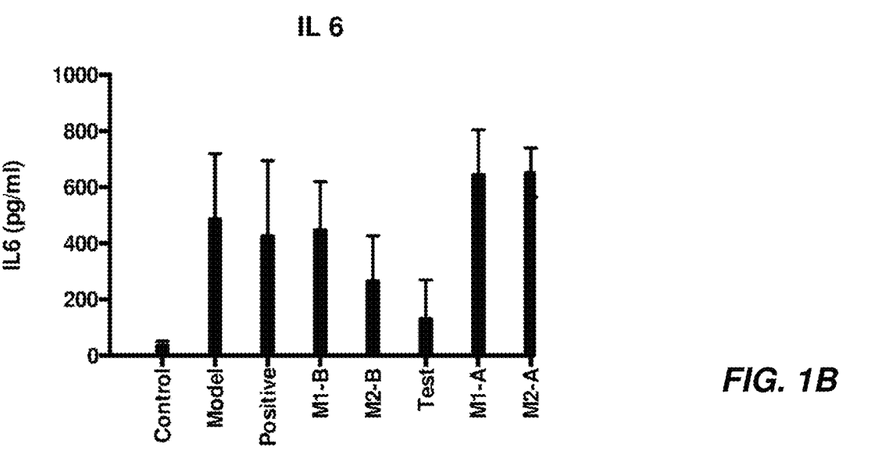
Figure 1C:
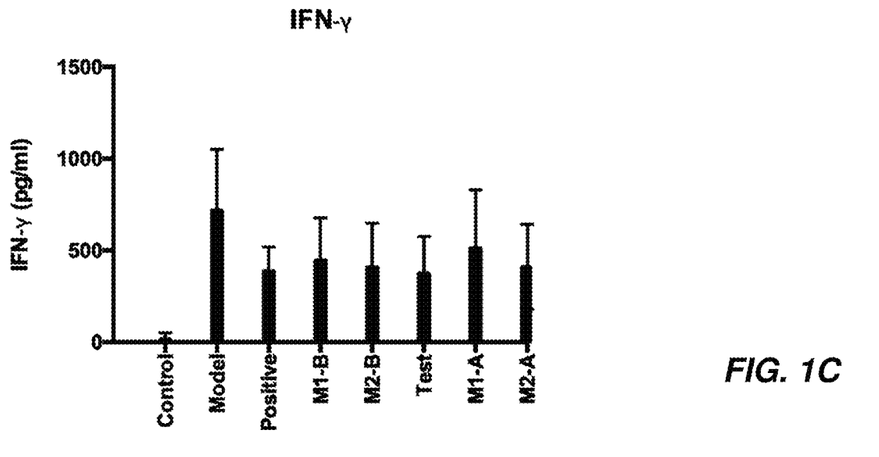
Figure 2A:
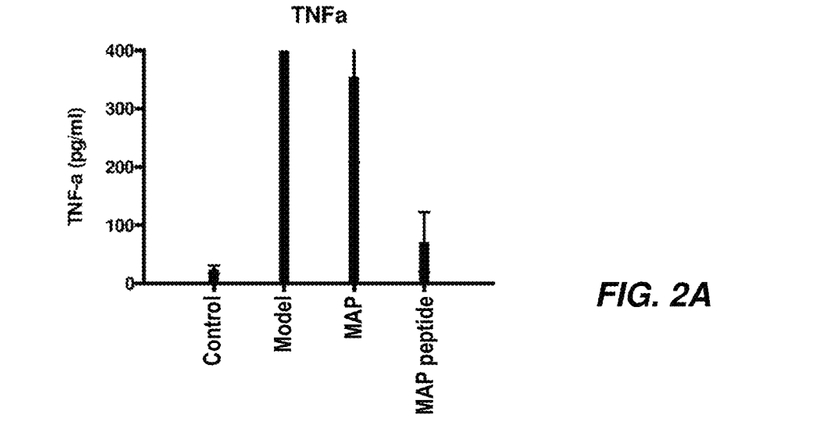
FIGS. 2A-C are graphs illustrating ELISA test results for various inflammatory markers obtained from exudates from air pouches induced in mice according to Example 2, including TNF-a (FIG. 2A), IL-6 (FIG. 2B), and IL-1β (FIG. 2C).
Figure 2B:
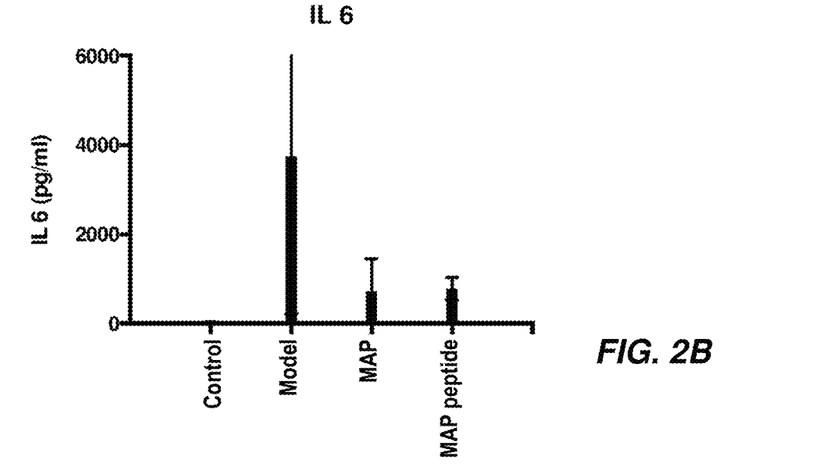
Figure 2C:
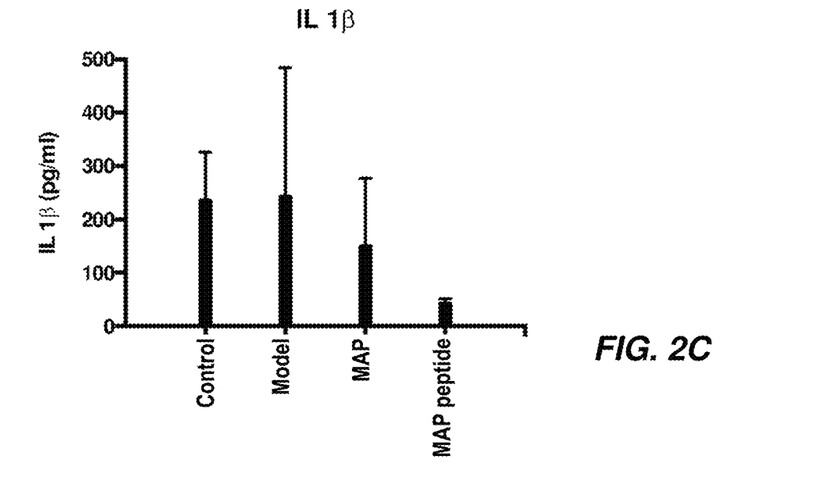
Figure 3:
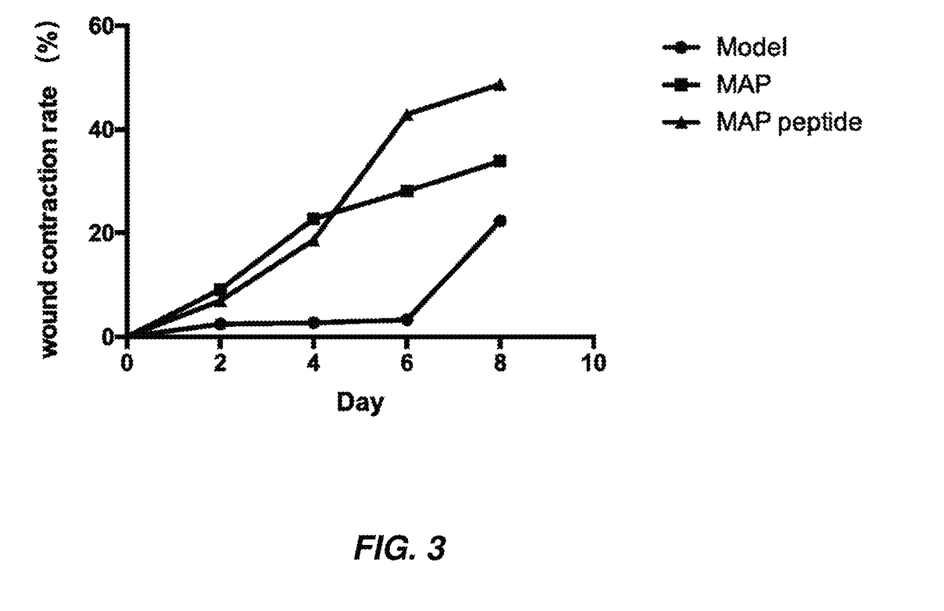
FIG. 3 is a graph that shows wound healing for various formulations in an acute wound mouse model.

The invention is illustrated by the following examples, in which FIGS. 1 and 2 present ELISA test results for various inflammatory markers obtained from exudates from air pouches induced in mice according to Examples 1 and 2, respectively, and FIG. 3 shows wound healing for various formulations in an acute wound mouse model.

EXAMPLES

Example 1

Air Pouch Model

Healthy adult male C57BL/6 mice weighing between 20 and 30 g were supplied by Nanjing Biomedical Research Institute (NBRI) of Nanjing University, China. Prior to any experiments being conducted, mice were housed under standardized conditions (at a constant temperature or 22±2° C., with alternating 12 hour periods of light and darkness), and were fed on a standard mouse diet with water, for about a week.

General anesthesia was induced using intraperitoneal 3% chloral hydrate (Sinopharm Chemical Reagent Co., Ltd., Shanghai, China); 1 mL/10 g of body weight). The hair of the entire dorsum was shaved and depilated 1 day before sterile air injection.

Air pouches were produced by subcutaneous injection of sterile air (5 mL) into the intrascapular area of the mice. After three days, another injection of air (3 mL) was performed to maintain the pouches. In order to induce acute inflammation, three days after this final injection, animals received an injection of sterile carrageenan solution (CP Kelco, Taixing, Jiangsu Province, China; 1%, 0.5 mL; produced by adding 0.1 g of carrageenan powder into a beaker containing 10 mL of 0.9% saline solution and stirring). Mice were pre-treated with test samples or vehicle 1 hour before and 23 hours after the carrageenan injection into the subcutaneous air pouch. Animals were sacrificed 24 hours after the carrageenan injection.

Skin biopsies were taken from the air pouches. A part of the biopsy was fixed in formalin (produced by adding ultra pure water to 50 mL of a 40% formaldehyde solution (Nanchang Rain Dew Experimental Equipment Co., Ltd., Nanchang, Hubei Provence, China) up to a total volume of 500 mL) and analyzed by histological embedding in paraffin wax, sectioning and staining.

The cavity was washed with 4 mL of sterile phosphate buffer solution (pH 7.4; prepared by dissolving 4 g of NaCl, 0.1 g of KCl, 1.749 g of $Na_2HPO_4.12H_2O$ and 0.1 g of $KH_2PO_4$ in ultrapure water, adjusting the pH to 7.4 with HCl and diluting with water to a total volume of 500 mL).

Exudates were collected and volumes were quantified. The total number of cells was determined with a haematocytometer (ADVIA 2120 Hematology System, Siemens Healthineers). The exudates were centrifuged at 3000 rpm for 10 minutes at 4° C., and the supernatants were collected and stored at −20° C. for ELISA analysis using standard ELISA test kits (Biolegend™ from Dakewe Biotech Co., Beijing, China or Abcam™, Abcam (Shanghai) Trading Co. Ltd, China) and an ELISA reader (SH-1000 Hitachi, Japan) for tissue necrosis factor alpha (TNF-α), interleukin 1 beta (IL-1β), interleukin 6 (IL-6), interleukin 10 (IL-10), prostaglandin E2 (PGE2), interferon gamma (IFN-γ) and 5-hydroxytryptamine (5-HT; serotonin).

After conducting some preliminary experiments to validate the model, an experiment was conducted in which mice were treated by administering test samples or vehicle in accordance with Table 1 below.

In Table 1, the M1-B, M2-B, M1-A and M2-A samples are MAP (Mefp-1) solutions of specified concentrations administered at different times relative to the carrageenan injection, as specified in the table. The solutions were prepared as follows. Blue mussels were harvested in the coastal area of Shandong Province, China. Mussel feet were collected, cut into small pieces and homogenized in an extraction buffer comprising 5% acetic acid in 4 mol/L of aqueous urea. The crude extracts were collected after centrifuging and then purified by liquid chromatography. The purified protein (semi-finished product; concentration 8 mg/mL; purity as measured by HPLC 91.72%; pH 4.2) was stored at 0° C. The solutions that were employed below were prepared by adding saline solution to this semi-finished product to obtain the concentrations described in Table 1.

Also in Table 1, "Test" is MAP Peptide, which was obtained from Innovagen AB, Sweden. The peptide was synthesized according to the relevant Mefp-1 amino acid sequence. The peptide powder was stored at −20° C. and dissolved in saline water at a concentration of 3.0 mg/mL, pH 5.5.

Dexamethasone (MedChemExpress, Shanghai, China) was obtained in powder form and dissolved in ultrapure water to obtain a solution with a concentration as described in Table 1.

All the substances listed in Table 1 were administrated topically by directly injecting into the air pouches.

TABLE 1

| Group | No. Mice | Drug concn. (mg/mL) | Dose/ mouse | Timing of Treatment (before carrageenan injection) |
|---|---|---|---|---|
| Control (air injection only) | 6 | normal saline | 4.5 mg (of NaCl) | n/a |
| Model (carrageenan injection) | 8 | normal saline | 4.5 mg (of NaCl) | 1 hour |
| Positive (dexamethasone) | 6 | 0.4 | 200 μg | 1 hour |
| M1-B (MAP) | 8 | 3 | 1.5 mg | 1 hour |
| M2-B (MAP) | 8 | 9 | 4.5 mg | 1 hour |
| Test (MAP Peptide) | 3 | 3 | 1.5 mg | 1 hour |
| M1-A (MAP) | 8 | 3 | 1.5 mg | 6 hours |
| M2-A (MAP) | 8 | 9 | 4.5 mg | 6 hours |

The volume of the exudate and the weight of air pouch wall (means±SD) for each group are tabulated in Table 2 below.

TABLE 2

| Group | Exudate volume (mL) | Pouch Wall Weight (g) |
|---|---|---|
| Control | 3.48 ± 0.12 | 0.68 ± 0.07 |
| Model | 3.76 ± 0.05 | 0.72 ± 0.09 |
| Positive | 3.3 ± 0.15 | 0.63 ± 0.09 |
| M1-B | 3.69 ± 0.08 | 0.77 ± 0.15 |
| M2-B | 3.61 ± 0.11 | 0.72 ± 0.08 |
| Test | 3.43 ± 0.06 | 0.60 ± 0.17 |
| M1-A | 3.65 ± 0.05 | 0.73 ± 0.08 |
| M2-A | 3.51 ± 0.11 | 0.7 ± 0.08 |

The total cell count and classification ($\times 10^6$/mL) is tabulated in Table 3 below.

TABLE 3

| Group | Leukocyte | Neutrophil | Monocyte |
|---|---|---|---|
| Control | 0.09 | 8.75 | 0.00 |
| Model | 3.34 | 260.03 | 74.17 |
| Positive | 3.49 | 285.97 | 62.53 |
| M1-B | 2.51 | 208.08 | 42.82 |
| M2-B | 2.77 | 251.38 | 25.92 |
| Test | 4.74 | 296.32 | 81.54 |
| M1-A | 2.53 | 194.48 | 58.59 |
| M2-A | 3.11 | 255.60 | 55.00 |

The histological specimens were analysed and an inflammation score, a motility score, an edema score and a motility score were estimated as follows.

The HE stained slices were observed under an optical microscope and were scored (1, 2 or 3 points) according to the perceived inflammation level (in cases showing only a small amount of inflammatory cells scattered in the area—1 point (mild); in cases where many inflammatory cells were observed—2 points (moderate); and, in cases with diffuse infiltration—3 points (severe)). A similar scoring system was employed for edema levels (3 points for most severe and 1 point for mild) after overall observation. Motility scores represented the density of neutrophils, which employed the same methodology as that employed for inflammatory cells.

TABLE 4

| Group | Inflammation score | Edema Score | Motility score | Sum |
|---|---|---|---|---|
| Control | 0.33 | 1.17 | 0.00 | 1.50 |
| Model | 2.17 | 2.67 | 1.17 | 6.00 |
| Positive | 1.83 | 1.67 | 0.67 | 4.17 |
| M1-B | 2.33 | 2.17 | 1.50 | 6.00 |
| M2-B | 1.83 | 1.83 | 1.17 | 4.83 |
| Test | 1.67 | 1.00 | 1.00 | 3.67 |
| M1-A | 1.33 | 1.17 | 0.67 | 3.17 |
| M2-A | 1.83 | 1.83 | 1.17 | 4.83 |

In the Control group, the pouch wall showed a small amount of scattered inflammatory cell infiltration, mild edema and no obvious neutrophil infiltration.

In the Model group, the pouch wall showed moderate to severe chronic inflammatory cell infiltration in the whole layer, moderate to severe edema and scattered neutrophil infiltration.

In the Positive control group, the pouch wall showed moderate chronic inflammatory cell infiltration, moderate interstitial edema and a small amount of neutrophil infiltration.

In the M1-B group, the pouch wall showed moderate to severe chronic inflammatory cell infiltration in the whole layer, moderate to severe edema and a small amount of neutrophil infiltration.

In the M2-B group, the pouch wall showed moderate chronic inflammatory cells infiltration in the whole layer, with moderate edema and a small amount of neutrophil infiltration.

In the Test (MAP Peptide) group, the pouch wall showed mild to moderate chronic inflammatory cell infiltration, interstitial edema a small amount of neutrophil infiltration.

In the M1-A group, the pouch wall showed mild chronic inflammatory cell infiltration, mild edema and some neutrophil infiltration.

In the M2-A group, the pouch wall showed moderate chronic inflammatory cell infiltration, moderate interstitial edema and a small amount of neutrophil infiltration.

The ELISA test results of the exudate for TNF-α, IL-6, IL-10 and IFN-γ always showed stable, high responses with a similar variation tendency. The results for TNF-α, IL-6 and IFN-γ (±SD) are tabulated in Table 5 below and shown graphically in FIGS. 1A-1C, respectively.

TABLE 5

| Group | TNF-α | IL-6 | IFN-γ |
|---|---|---|---|
| Control | 8.42 ± 5.65 | 36.95 ± 14.22 | 18.34 ± 33.65 |
| Model | 143.60 ± 65.56 | 487.97 ± 231.99 | 718.51 ± 331.12 |
| Positive | 65.08 ± 7.70 | 428.05 ± 267.27 | 388.83 ± 130.02 |
| M1-B | 187.18 ± 123.01 | 448.52 ± 172.03 | 445.90 ± 231.30 |
| M2-B | 194.27 ± 112.77 | 265.85 ± 160.85 | 411.03 ± 236.68 |
| Test | 58.49 ± 28.72 | 132.63 ± 137.34 | 377.31 ± 198.68 |
| M1-A | 192.87 ± 125.19 | 646.61 ± 158.50 | 512.42 ± 319.29 |
| M2-A | 219.37 ± 101.10 | 653.09 ± 87.78 | 412.10 ± 231.74 |

Example 2

Air Pouch Model II

Essentially the same procedure as that described in Example 1 above was followed, to treat mice by administering test samples or vehicle in accordance with Table 6 below.

In this example, MAP Peptide powder was dissolved in saline water at a concentration of 0.6 mg/mL at pH 5.5. Then 0.5 mL of the solution was injected into each air pouch in the group.

TABLE 6

| Group | No. Mice | Drug concn. (mg/mL) | Dose/ mouse | Timing of Treatment (before carrageenan injection) |
|---|---|---|---|---|
| Control | 5 | Normal saline | 4.5 mg (of NaCl) | n/a |
| Model | 5 | Normal saline | 4.5 mg (of NaCl) | 1 hour |
| MAP | 5 | 0.6 | 300 μg | 1 hour |
| MAP Peptide | 5 | 0.6 | 300 μg | 1 hour |

The histological specimens were analyzed and scored as outlined in Example 1 above, as shown in Table 7.

TABLE 7

| Group | Inflammation Score | Edema Score | Fibroplastic proliferation score | Sum |
|---|---|---|---|---|
| Control | 1 | 1.2 | 0.8 | 2.2 |
| Model | 2.2 | 1.8 | 0.6 | 4 |
| MAP | 2 | 1.2 | 0.4 | 3.2 |
| MAP Peptide | 1.6 | 1.8 | 0.2 | 3.4 |

In this example, ELISA analysis was carried out for TNF-α, IL-6, and IL-1β, which are shown graphically in FIGS. 2A-2C, respectively. The results showed that MAP Peptide had very strong anti-inflammatory effects.

Example 3

Acute Wound Model 6-8 weeks old male C57BL/6 mice were supplied by Changzhou Ovens Experimental Animal Co. Ltd (Changzhou, Jiangsu Province, China). Prior to any experiments being conducted, mice were housed under standardized conditions (at a constant temperature of 22±2° C., with alternating 12 hour periods of light and darkness), and were fed on a standard mouse diet with water, for about a week.

General anesthesia was induced using intraperitoneal 3% chloral hydrate (1 mL/10 g of body weight). The hair on the back was shaved by a baby hair shaver and depilated with cream. The skin area was wiped and sterilized with 75% alcohol twice.

An EMS skin biopsy punch (Electron Microscopy Sciences, P.O. Box 550, 1560 Industry Road, Hatfield, PA, USA) with 8 mm diameter was used to make a round wounds on each side of the midline of the back. The full thickness of skin was removed and the depth of the wound reached the fascia. Wounds were left open without a suture.

Different drugs were administered topically at 50 μL/wound, once daily from Day 0 to Day 12, as show in Table 8 below. The control group did not have a wound inflicted. The model group was given same amount of normal saline. There were 12 mice in each group.

For this experiment, MAP Peptide was obtained from GL Biochem (Shanghai) Ltd. The peptide powder was stored at −20° C. and dissolved in saline at a concentration of 33 μg/mL.

20 μL of respective solutions were applied onto each wound surface in the relevant groups.

TABLE 8

| GROUP | Day 4 | Day 7 | Day 14 | MEANING | DOSAGE |
|---|---|---|---|---|---|
| Control | 4 | 4 | 2 | saline | / |
| Model | 4 | 4 | 2 | Model + saline | / |
| MAP | 4 | 4 | 2 | Model + MAP | 5 μg/wound |
| MAP Peptide | 4 | 4 | 2 | Model + MAP Peptide | 6.57 μg/wound |

Wounds were dressed with gauze and transparent dresser after drug administration. Photographs were taken for each wound every other day from Day 0. Photos were scanned into a computer, and wound areas calculated using ImageJ image analysis software (National Institutes of Health, China).

Photographs were taken for each wound every other day from Day 0. Wound healing was calculated by the wound contraction ratio (WCR)

$$WCR=(A_0-A_t)/A_0\times 100\%$$

where $A_0$ and $A_t$ refer to the initial area at Day 0 and the wound area at the date of measurement (time t), respectively.

The effects of MAP Peptide on wound healing are show in Table 9 and FIG. 3, which show the WCR in different groups (±SD in the case of Table 9).

TABLE 9

| Group | Model | MAP | MAP Peptide |
|---|---|---|---|
| Day 0 | 0.00 ± 0 | 0.00 ± 0 | 0.00 ± 0 |
| Day 2 | 2.46 ± 1.87 | 9.11 ± 0.65 | 6.99 ± 2.02 |
| Day 4 | 2.72 ± 0.67 | 22.70 ± 0.31 | 18.65 ± 1.87 |
| Day 6 | 3.25 ± 1.02 | 28.08 ± 0.54 | 42.91 ± 0.57 |
| Day 8 | 22.34 ± 0.55 | 33.90 ± 0.61 | 48.73 ± 1.65 |

The above data show that MAP Peptide had a stronger effect on wound healing than MAP. An improvement rate for MAP Peptide, defined as (WCR MAP Peptide Group−WCR MAP Group)/ WCR MAP Group×100%.

at Day 6 is 52.96% greater than the MAP group.

3 mice were sacrificed by cervical vertebra dislocation, respectively, at Day 4 and Day 7 post-wound in each group. 2 mice were kept for 14 days to observe the wound healing. The wound tissue was taken by the same biopsy punch used to create the wound. Then 5 mm of tissue was cut off from the center of the sample and preserved in 10% neutral buffered formalin (Nanchang Rain Dew Experimental Equipment Co., Ltd., Nanchang, Hubei Provence, China), and analyzed by histological embedding (HE) in paraffin wax, sectioning and staining.

HE and Masson stained paraffin sections were observed under an optical microscope. Skin regeneration, fibroblastic proliferation, collagen regeneration scores and inflammation scores were estimated.

The rest of the samples were stored at −80° C. for other indexes detection. Tissue was cut into small pieces and added liquid nitrogen to increase the brittleness. 9 mL of normal saline was added to 1 g of tissue, which was then ground using a Tissuelyser (Shanghai Jingxin Industrial Development Co., Ltd., Shanghai, China) at 55 Hz for 60 seconds and centrifuge at 8000 rpm for 10 minutes at 4° C.

The supernatant was collected and the extracted protein was used for ELISA analysis by using standard ELISA test kits and an ELISA reader (SH-1000 Hitachi, Japan) for vascular endothelial growth factor (VEGF) and hydroxyproline (Hyp) assay. The ELISA kits were purchased from Beijing 4A Biotech Co., Ltd. (Beijing, China).

Example 4

MAP Peptide Liquid Spray to Treat Polymorphous Light Eruption.

MAP Peptide was dissolved in water for injection (WFI; prepared from TC-RO-0.25T/h-2 water treatment system, Yangzhou Tiancheng Water Treatment Devices & Engineering Co., Ltd., Yangzhou, China). The concentration of the solution was 1.5 mg/mL. The solution was loaded into a spray device.

Enrolled subjects in the study were diagnosed with polymorphous light eruption (an inflammatory condition characterized by a rash caused by sun exposure in people who have developed sensitivity to sunlight). Prior to treatment, the patients presented symptoms including skin redness, papules, itching and swelling.

Subjects were required to use the liquid spray in the morning and the evening after facial cleansing.

The use of the MAP Peptide spray relieved itching within 1 minute and inhibited malaise. Most of the observed erythema was alleviated within 1 minute. Itch was completely relieved within 1 minute for 50% of the tested subjects. The erythema of 50% subjects completely disappeared in a few hours.

We have observed that, compared to treatment with a similar solution comprising MAP (spray of same concentration in WFI), MAP Peptide shows a much more rapid erythema alleviation efficiency in this condition.

Example 5

MAP Peptide Spray (to Treat Common Cold)

MAP Peptide (30 mg) was dissolved in 10 mL of water. Trypsin (30 mg; Sichuan Deebio Pharmacutical Co. Ltd., Guanhan, China) was dissolved in another 10 mL of water.

Calcium chloride (0.1 g), ethanol (0.5 g), water-soluble menthol (0.01 g), lactic acid 0.01 g and glycerol (30 g) (all Sinopharm Chemical Reagent Co. Ltd), were mixed together in 49.32 mL of water.

The solutions containing MAP Peptide and trypsin were added to the mixture with stirring to provide a liquid for spraying.

Example 6

MAP Peptide/Trpysin Aerosol for Inhalation

An aerosol formulation was prepared essentially as described in Example 5 above, from 20 mg of MAP Peptide and 30 mg of trypsin, this time without glycerol and in a total of 99.32 mL of water.

The invention claimed is:

1. A method of cosmetic treatment of inflammation, of an inflammatory disorder, and/or of a disorder or condition characterized by inflammation, which method comprises:
   administering a cosmetic composition comprising an isolated decapeptide consisting of the amino acid sequence of Ala-Lys-Pro-Ser-Tyr-Hyp-Hyp-Thr-DOPA-Lys (SEQ ID NO: 1) or a cosmetically-acceptable salt thereof in admixture with a cosmetically-acceptable adjuvant, diluent or carrier, to a patient in need of such treatment.

2. The method as claimed in claim 1, wherein the inflammatory disorder is selected from psoriasis, acne, eczema and dermatitis.

3. The method as claimed in claim 2, wherein the dermatitis is atopic dermatitis.

4. The method as claimed in claim 1, wherein the condition or disorder characterized by inflammation is a wound or a burn.

5. The method as claimed in claim 4, wherein the wound is selected from an abrasion, a scratch, an incision, a laceration, a skin puncture, an avulsion, a bruise, a skin graft, a blister, an ulcer, chilblains and frostbite.

6. The method as claimed in claim 4, wherein the wound is a hard to heal ulcer.

7. The method as claimed in claim 1, wherein the inflammatory disorder comprises erythema, redness, swelling, edema, bullous pemphigoid, exudation of subcutaneous tissue fluid.

8. The method as claimed in claim 1, wherein the inflammatory disorder results from an infection or a food allergy, or comprises herpes, a drug eruption, a polymorphous light eruption, sunburn, an early manifestation of a skin cancer, pathological hair loss, chemo rash, erythema multiforme, folliculitis or external otitis.

9. The method as claimed in claim 8, wherein the infection is a viral or a bacterial infection, or the early manifestation of a skin cancer is an erythema-like skin lesion.

10. The method as claimed in claim 1, wherein said administering prevents treats a physiological reaction that results from inflammation or a wound healing process.

11. The method as claimed in claim 10, wherein the physiological reaction comprises scarring or melanin pigmentation.

12. The method as claimed in claim 1, wherein said administering suppressing a disorder associated with melanin pigmentation.

13. The method as claimed in claim 12, wherein the disorder is selected from chloasma, freckles, melanosis, malar rash, a skin cancer with melanoma, and a chromatosis that is caused by exposure to the sun or a skin disease.

14. The method as claimed in claim 1, wherein said administering is carried out by direct topical administration to the patient's skin.

* * * * *

UNITED STATES PATENT AND TRADEMARK OFFICE
CERTIFICATE OF CORRECTION

PATENT NO. : 12,129,313 B2
APPLICATION NO. : 17/350795
DATED : October 29, 2024
INVENTOR(S) : Samuelsson and Gu It is certified that error appears in the above-identified patent and that said Letters Patent is hereby corrected as shown below:

In the Claims

At Claim 10, Column 20, Line 5, please delete "prevents".

Signed and Sealed this
Third Day of December, 2024

Katherine Kelly Vidal
*Director of the United States Patent and Trademark Office*